United States Patent [19]

Apffel

[11] Patent Number: 4,767,428
[45] Date of Patent: Aug. 30, 1988

[54] NITROGEN REMOVAL SYSTEM
[75] Inventor: Fred Apffel, Houston, Tex.
[73] Assignee: Flexivol, Inc.
[21] Appl. No.: 848,381
[22] Filed: Apr. 4, 1986

Related U.S. Application Data

[60] Continuation-in-part of Ser. No. 598,051, Apr. 9, 1984, Pat. No. 4,597,788, which is a division of Ser. No. 356,918, Mar. 10, 1982, Pat. No. 4,456,460.

[51] Int. Cl.[4] ................................................ F25J 3/02
[52] U.S. Cl. .......................................... 62/24; 62/34; 62/40; 62/42; 62/44
[58] Field of Search ............... 62/9, 11, 23, 24, 27–34, 62/40, 42, 44

[56] References Cited

U.S. PATENT DOCUMENTS

| | | | |
|---|---|---|---|
| 3,592,015 | 7/1971 | Streich et al. | 62/28 |
| 3,596,472 | 8/1971 | Streich | 62/40 |
| 4,112,700 | 9/1978 | Forg | 62/40 |
| 4,274,850 | 6/1981 | Becker | 62/38 |
| 4,411,677 | 10/1983 | Pervier et al. | 62/40 |
| 4,456,460 | 6/1984 | Apffel | 62/40 |

Primary Examiner—Ronald C. Capossera
Attorney, Agent, or Firm—David M. Ostfeld

[57] ABSTRACT

A process for separating a nitrogen rich hydrocarbon stream is disclosed. The process includes cooling the stream in a series of indirect heat exchanges to separate successively lighter components from heavier components of the stream. After the first cooling stage, the stream is separated into a heavy component stream and a light component stream. The heavy component is distilled to form a heavy product stream and a first methane rich gas stream. The lighter component stream is successively cooled and split into a second methane rich gas stream and a nitrogen rich, low heating value stream.

7 Claims, 1 Drawing Sheet

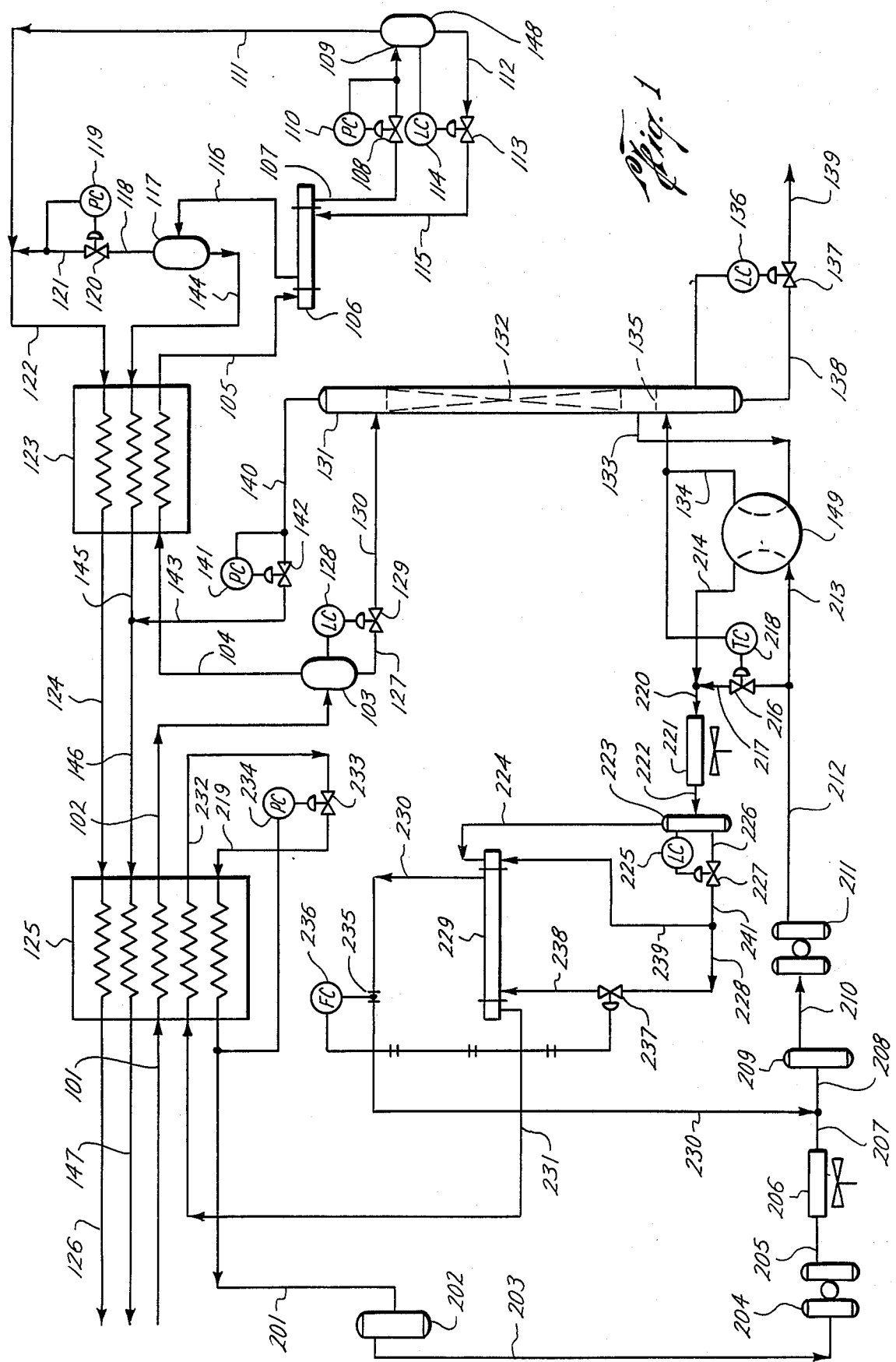

NITROGEN REMOVAL SYSTEM

CROSS REFERENCE TO RELATED APPLICATIONS

This application is a substitute for U.S. Pat. No. 742,723, filed June 7, 1985, by Mr. Fred Apffel, entitled "Nitrogen Removal System" now abandoned and is a continuation-in-part of U.S. Application Ser. No. 598,051, filed Apr. 9, 1984, by Fred Apffel, entitled "Process For Recovering Ethane, Propane and Heavier Hydrocarbons From a Natural Gas Stream" now U.S. Pat. No. 4,597,788, which is a division of U.S. patent application Ser. No. 356,918, filed Mar. 10, 1982, by Mr. Fred Apffel, entitled "Process for Recovering Ethane, Propane and Heavier Hydrocarbons from a Natural Gas Stream", now U.S. Pat. No. 4,456,460.

TECHNICAL FIELD

The invention relates generally to processes for economically separating valuable hydrocarbons from hydrocarbon streams containing large concentration of nitrogen. More specifically it relates to an economical refrigeration process for producing a low heating value nitrogen rich stream that is used as fuel, a saleable methane gas stream and recovery of the ethane, propane and heavier hydrocarbons as a liquid.

BACKGROUND ART

Natural gas is obtained from underground reservoirs and pumped through pipelines to various industrial and commercial consumers. Much of the natural gas is utilized for heating purposes and, accordingly, requires a BTU content of only 900 to 1000 BTU per m.c.f. A natural gas stream composed mainly of methane and ethane is sufficient to achieve such heating values. However, much of the natural gas obtained from underground reservoirs contains substantial quantities of nitrogen and hydrocarbon components, such as ethane, propane, pentane and butane, which are heavier than methane. The heavier hydrocarbon components are industrially valuable in many processes, and accordingly, individual separation of them from the methane as a product is highly desirable. However, removal of the heavier hydrocarbons leaves a nitrogen and methane mixture that will not sell as such because of its low BTU content. Based on this problem, the nitrogen must be separated from the methane. The present invention provides a means of separating the nitrogen as a low BTU fuel stream and production of a methane product that meets the 900 to 1000 BTU requirements.

None of the prior art shows the process of the present invention for producing a nitrogen rich low BTU fuel, a methane product meeting the BTU requirements and recovery of the ethane-and-heavier hydrocarbons as product liquids.

It is an object of the present invention to teach a method of cryogenic separation that lowers overall fuel consumption or horsepower to produce the cryogenic temperatures required.

It is a further object of the present invention to teach a method of cryogenic separation that permits broad latitude of operation. In particular, the ability to adjust the refrigerant composition to match the cooling and condensing characteristics of the feed in the process permits a degree of freedom not available in other process schemes more rigidly fixed or restrained by equipment designed for a specific process. This feature permits the process to process feed gases having a broad range of composition levels, without suffering in recovery efficiency.

It is yet another object of the present invention to teach a method of cryogenic separation where the turndown capability is essentially unlimited.

It is yet a further object of the present invention to teach a method of cryogenic separation wherein the reduction in ethane-and-heavier hydrocarbon recovery efficiency is not nearly as pronounced on increasing through-put as it is with other systems.

It is yet another object of this invention to teach a method of separating nitrogen from methane and producing methane product having a BTU content of 900 to 1000 BTU and recovery of the ethane, propane and heavier hydrocarbons as a liquid product.

DISCLOSURE OF THE INVENTION

A process and apparatus for separating a feed stream of hydrocarbons having large concentrations of nitrogen into a low heating value nitrogen rich fuel stream, a saleable methane gas stream and heavier liquid hydrocarbons is disclosed. A multicomponent inlet feed stream is cooled in indirect heat exchange and flashed to further lower temperature and to separate liquids from vapors. The vapors are further cooled in a dual indirect heat exchange with all ready processed gas, and flashed twice in sequence, while exchanging with the vapors entering the first of the flash sequence. The liquids which form the methane rich stream, and vapors, which form the nitrogen rich stream, from the second and first flash are further exchanged with the inlet vapor stream. The liquid stream is distilled with the vapors from the distillation joining the methane rich stream and the liquids from the distillation being the heavier liquid hydrocarbons.

BRIEF DESCRIPTION OF THE DRAWINGS

For a further understanding of the nature and objects at the present invention, reference is made to the following drawing in which like parts are given like reference numerals, and wherein:

FIG. 1 is a schematic of the preferred embodiment of the present invention.

DESCRIPTION OF THE PREFERRED EMBODIMENT

Process Stream

As shown in FIG. 1, process inlet or feed gas enters the process at stream 101. Typical feed gas streams are set out in the following Table I, below.

TABLE I

| Feed Gas Range of Composition | |
|---|---|
| Component | Mol % |
| Nitrogen | 10–50 |
| Carbon Dioxide | 0.1–2 |
| Methane | 65–85 |
| Ethane | 0–10 |
| Propane | 0–10 |
| I—Butane | 0–5 |
| N—Butane | 0–5 |
| I—Pentane | 0–4 |
| N—Pentane | 0–4 |
| Hexane | 0–3 |

The pressure range of the inlet gas is 15 to 1500 psia, with a temperature range of 50° to 150° F.

The inlet is dehydrated (not shown) and the carbon dioxide is removed (not shown) prior to entering stream 101.

Dehydration, or removal of any moisture that the inlet gas may contain is imperative. Even slight amounts of water in the gas stream at the cyrogenic temperatures required to separate the nitrogen from the hydrocarbons will form hydrates and freeze. This will subsequently plug up the equipment and piping.

Similarly, the carbon dioxide must be removed. It will also solidify at the temperatures that are required for this separation.

Dehydration is accomplished by processing the gas through a vessel, not shown, containing molecular sieve material. The molecular sieve material is porous and water, being a smaller molecule than the hydrocarbons, is preferentially absorbed into its pores. The gas exits the dehydration unit essentially free of moisture. The molecular sieve bed becomes saturated with water after a period of time and has to be regenerated. Therefore, two adsorption vessels are required. One is always in absorption service while the other is being regenerated.

The regeneration is achieved by recycling a slip stream of the dry residue gas. Approximately 8 to 10 percent of the through-put gas is required for this purpose. The regeneration gas is compressed and heated to approximately 550° F. and processing through the dehydrator being regenerated, driving the moisture from the molecular sieve. This hot regeneration gas bearing the desorbed moisture is subsequently cooled, and the major part of the water is condensed from the gas. The water is dumped to the process sewer, and the regeneration gas is recycled to the main residue-gas stream. After the water has been removed from the molecular sieve, the heater is bypassed or turned off, and the dehydrator is cooled to ambient or inlet gas temperature, using the regeneration gas.

The carbon dioxide is removed in an amine absorption system or other suitable treating system.

The feed gas in stream 101 is fed to the multi-pass brazed aluminum exchanger 125 where it is cooled to a temperature level of $-40°$ to $-150°$ F. The temperature level is established by the feed composition being warmer for gas streams containing more of the heavier hydrocarbons. The purpose is to reduce this temperature to a point where the heavier hydrocarbons, ethane-and-heavier, condense and may be extracted separately from the system. The feed gas exits the exchanger 125 in stream 102 and flows to the vapor-liquid separator 103. The separated vapor from separator 103 flows in stream 104 to the multi-pass brazed aluminum exchanger 123 and is cooled to a temperature level of $-180°$ to $-200°$ F. This cold fluid is further reduced in temperature to $-220°$ to $-240°$ F. by cross-exchange of a colder liquid in exchanger 106. The cold liquid exits the exchanger 106 in stream 107 and flows through the pressure reducing valve 108. The amount of reduction in pressure is controlled by pressure controller 110. This pressure is varied from 25 to 200 psi, depending on the amount of nitrogen in the feed gas. The vapor/liquid fluid flows from the control valve 108 via stream 109 to the vapor liquid separator 148. The vapor from separator 148 exits the separator 148 via stream 111. The liquid from this separator 148 flows in stream 112 to the liquid level valve 113 and on to stream 115. The liquid is partially evaporated in exchanger 106 where it cross-exchanges with the warmer feed in stream 105. The fluid is subsequently fed to the vapor-liquid separator 117. The vapor from separator 117 exits in stream 118 flowing through the pressure control valve 120 into stream 121. The back pressure is maintained by the pressure controller 119. The vapor in stream 121 is combined with the vapor in stream 111 and fed to the exchanger 123 and cross-exchanged with the warmer feed in stream 104. This gas exits exchanger 123 in stream 124 and flows to the exchanger 125 and is further warmed to a temperature of 60° to 120° F. in exchanger 125.

The liquid from the vapor liquid separator 117 exits in stream 144 and flows to the exchanger 123 to be evaporated as it is cross-exchanged with the warmer feed gas in stream 104. The vapor exits exchanger 123 at temperature of $-130°$ to $-90°$ F. in stream 145. It is recombined with gas in stream 143 from the distillation tower 131. The combined gas enter stream 146 flowing to the exchanger 125 to cross-exchange with the warmer feed in stream 101. It exits this exchanger in stream 147 for further processing.

The liquid condensed in the vapor-liquid separator 103 exits in stream 127 flowing to the distillation tower 131 to distill the lighter hydrocarbons from the heavier components. The flow is controlled by the level control valve 129 and the level controller 128. Heat is provided to the bottom of the distillation tower 131 in the reboiler 149. A liquid stream is collected in the chimney tray 135 flowing in stream 133 to the reboiler 149 where it is heated and partially evaporated and returned to the tower in stream 134. The heat is provided by the compressed refrigerant gas in stream 213. Control of the amount of heat is maintained with the temperature control valve 216 and temperature controller 218.

The returning vapor and liquid in stream 134 are separated in the bottom of the distillation tower 131, the vapor flowing up the tower 131 through packing 132 and exiting the tower 131 via stream 140. The flow of the vapor, and pressure in column 131, is controlled by valve 142 and pressure controller 141. The vapor exits valve 142 in stream 143 where it combines with the vapor in stream 145 as discussed above. The liquid leaves the bottom of the distillation tower in stream 138 as product. The amount of liquid is controlled by the liquid control valve 137 and liquid level controller 136.

Refrigeration Cycle

The process uses an indirect refrigerant system to reduce the feed-gas stream to the desired cryogenic temperature. The refrigerant is compressed, heat of compression removed, cooled and condensed, expanded across a valve, and evaporated as it transfers the cold energy to the feed-gas stream. The system is compounded by a multi-path scheme devised to improve its efficiency. Additionally, the cold or evaporating refrigerant provides part of the energy to condense and sub-cool the warm refrigerant to the desired temperature.

The refrigerant is made up of a mixture of hydrocarbons. These include, preferably, methane, ethylene, propane, butanes, and pentane described above. The concentration of these components may be adjusted to match the cooling and condensing characteristics of the feed gas being refrigerated and the cryogenic temperature requirement. The composition range of the components of the refrigerant is set out in Table II, below:

TABLE II

| Refrigerant Composition Range | |
|---|---|
| | Mol % |
| Nitrogen | 0–5 |

TABLE II-continued

| Refrigerant Composition Range | |
|---|---|
| | Mol % |
| Methane | 10–50 |
| Ethane | 20–50 |
| Ethylene | |
| Propane | 15–20 |
| I—Butane | 0–15 |
| N—Butane | 0–15 |
| I—Pentane | 0–15 |

The components are adjusted to minimize the area between the warm condensing and cold evaporating streams, as illustrated in FIG. 1. Additionally, the refrigerant flow rate and refrigerant compression ratio may be varied to further adjust the refrigerant system. Each of the variables is optimized to produce the most efficient, economic refrigerant design for the feed gas being processed.

The operation of the refrigerant system is fully automated and easy to control. However, the addition of refrigerant components is not automatic. To determine the addition of refrigeration components, a multipoint recorder may be provided, which produces equally spaced temperatures along the path of the warm and cold refrigerant streams in the Feed/Refrigerant Exchanger. A plot of this data will reveal the area where these curves are too close together, as well as the temperature level. If it occurs in the area where ethylene evaporates, for example, this refrigerant should then be added. Adding a couple of refrigerant bottles similar in size to an oxygen or acetylene bottle will normally correct any problem. The system is not overly sensitive to the refrigerant composition. A chromatograph may also be provided to determine the refrigerant composition from time to time. The operator can adjust the refrigerant accordingly.

Each stage includes a refrigerant compressor suction scrubber and a compressor. The sizes of the scrubbers depend upon the size of the refrigerant system. They are typically fabricated units and can be purchased from any number of vendors including Watts Company, McIver and Smith, and Taylor Tank. The compressors are preferably reciprocating compressor, such as that built by Ingersoll Rand Co., Worthington Corp. and Clark Industries. It is recognized that the compressors could also be a centrifugal but with overall lower horsepower efficiency.

The first stage of compression includes stage 204. Compressor 204 should be sized to raise the stream pressure from an inlet pressure of 20 to 100 psia in stream 203 to a discharge pressure of 100 to 250 psia in stream 205. The discharge stream 205 from the first compression stage 204 enters the first stage after cooler 206. The outlet of the after cooler 206 exits in stream 207 and joins returning refrigerant stream 230. They are combined in stream 208 and flow into a compressor suction scrubber 209 to ensure that any entrained liquid is not fed to the second stage compressor 211. The second stage compression 211 should be sized to raise the inlet pressure of 100 to 250 psia in stream 210 to a pressure level at the outlet 212 of 250 to 600 psia with a temperature rise from the inlet 210 of 80° to 120° F. to an outlet 212 of 250°–380° F.

Those skilled in the art will recognize that there are several methods of obtaining adequate compression of refrigerant gases in a two stage process. The present invention should not be limited to any particular physical design of the two-stage refrigerant system. The alternative examples given above are given merely as illustration and are not intended to limit the scope of the invention.

The heat energy in stream 212 is utilized in the distillation reboiler 149 via stream 213. It exits reboiler 149 in stream 214. Controls of the heat extraction from the stream 213 is provided with the by-pass stream 215 and the temperature control valve 216. The temperature controller 218 causes the temperature control valve to open or close and maintain a constant distillation bottoms temperature of 100° to 150° F. Further heat is removed in the final discharge cooler 221 where the stream temperature of stream 220 is reduced to a level of 100° to 120° F.

The stream 222 leaving the discharge cooler 221 flows to the discharge separator 223 where the vapor and liquid are separated in the separator 223. The liquid flows from the separator 223 to the liquid control valve 227. The liquid control valve 227 maintains the liquid level in the separator 223. Part of the liquid flows to the refrigerant exchanger 229 in stream 228 and 238. The amount of flow is controlled by the flow control valve 237, flow controller 236 and orifice 235. The control valve also reduces the pressure to the compressor interstage level and reduces the temperature because of the Joule-Thomson effect to 0°–60° F. The cold fluid in stream 238 is cross-exchanged with the warmer refrigerant in stream 224 and 239 to reduce the warm refrigerant temperature to 50°–80° F. in the refrigerant exchanger 229. The vapor from the refrigerant exchanger 229 in stream 230, is recombined in stream 208 with stream 207. The remaining liquid in stream 241 flows in stream 239 to the refrigerant exchanger 229 to be recombined with the vapor in stream 224 to be cooled to a temperature of 50°–80° F. and exits in stream 231.

Stream 231 flows to the multi-pass brazed aluminum exchanger 125 and is further cooled to −100° to −180° F. in stream 232. Stream 232 is reduced in pressure by the pressure control valve 233 to the first stage compressor 204 suction pressure. This pressure is controlled by the pressure controller 234. A drop in temperature of 20° to 30° F. can be expected because of the Joule-Thomson effect. This colder refrigerant in stream 219 returns to the multi-pass brazed aluminum exchanger 125 to cross-exchange with the warmer refrigerant and feed gas in streams 231 and 101 respectively. The colder refrigerant exits the multi-pass exchanger 125 as stream 201 returning to the first stage of compression 202 to complete the refrigerant cycle as feed stream 203.

Example

The following is given as an example that illustrates, but should not limit, the present invention. The example is given in the form of Tables III and IV which shows steady state process and refrigerant flows and theoretical tray flows, respectively, and where the stream numbers correspond to the stream numbers of FIG. I. The use of "V" and "L" before a stream number denotes the vapor and liquid phase of the stream respectively. The number "2" before a stream number denotes a two-phase stream of liquid and vapor.

| STREAM NO | | | | | | | | | | | |
|---|---|---|---|---|---|---|---|---|---|---|---|
| | 101 | 102 | 104 | 105 | 107 | 109 | 112 | 116 | 111 | 121 | 122 |
| PHASE | V | 2 | V | L | L | 2 | L | 2 | V | V | V |
| | MATERIAL BALANCE EXAMPLE (FEED GAS) | | | | | | | | | | |
| N2 | 281.73 | 281.73 | 276.00 | 276.00 | 276.00 | 276.00 | 56.54 | 56.54 | 219.46 | 41.03 | 260.49 |
| CO2 | 5.25 | 5.25 | 3.87 | 3.87 | 3.87 | 3.87 | 3.85 | 3.85 | 0.02 | 0.02 | 0.04 |
| CH4 | 304.52 | 304.52 | 277.12 | 277.12 | 277.12 | 277.12 | 232.66 | 232.66 | 44.46 | 32.90 | 77.36 |
| C2H6 | 35.00 | 35.00 | 13.39 | 16.39 | 16.39 | 16.39 | 16.39 | 16.39 | 0.01 | 0.01 | 0.02 |
| C3H8 | 17.86 | 17.86 | 2.33 | 2.33 | 2.33 | 2.33 | 2.33 | 2.33 | 0.00 | 0.00 | 0.00 |
| IC4H10 | 2.96 | 2.96 | 0.12 | 0.12 | 0.12 | 0.12 | 0.12 | 0.12 | 0.00 | 0.00 | 0.00 |
| NC4H10 | 4.60 | 4.60 | 0.12 | 0.12 | 0.12 | 0.12 | 0.12 | 0.12 | 0.00 | 0.00 | 0.00 |
| IC5H12 | 1.90 | 1.90 | 0.01 | 0.01 | 0.01 | 0.01 | 0.01 | 0.01 | 0.00 | 0.00 | 0.00 |
| NC5H12 | 1.58 | 1.58 | 0.01 | 0.01 | 0.01 | 0.01 | 0.01 | 0.01 | 0.00 | 0.00 | 0.00 |
| IC6H14 | 1.31 | 1.31 | 0.00 | 0.00 | 0.00 | 0.00 | 0.00 | 0.00 | 0.00 | 0.00 | 0.00 |
| | 656.71 | 656.71 | 572.97 | 575.97 | 575.97 | 575.97 | 312.02 | 312.03 | 263.95 | 73.96 | 337.91 |
| TEMP, D-F | 100.00 | −100.00 | −100.00 | −192.80 | −200.00 | −260.00 | −260.00 | −240.00 | −260.00 | −240.00 | −260.00 |
| PRESS, PSIA | 700.00 | 695.00 | 695.00 | 695.00 | 695.00 | 70.00 | 70.00 | 65.00 | 70.00 | 65.00 | 65.00 |
| MASS, LB/HR | 15652 | 15652 | 12959 | 12959 | 12959 | 12959 | 6097 | 6097 | 6862 | 1679 | 8540 |
| MOL WT | 23.83 | 23.83 | 22.50 | 22.50 | 22.50 | 22.50 | 19.54 | 19.54 | 25.99 | 22.69 | 25.28 |

| STREAM NO | | | | | | | | | | | | | |
|---|---|---|---|---|---|---|---|---|---|---|---|---|---|
| | 124 | 126 | 144 | 145 | 143 | 146 | 147 | 127 | 140 | 138 | 201 | 203 | 205 |
| PHASE | V | V | L | V | V | V | V | L | V | L | V | V | V |
| | MATERIAL BALANCE EXAMPLE (FEED GAS) | | | | | | | | | | MATERIAL BALANCE EXAMPLE (REFRIGERANT) | | |
| N2 | 260.49 | 260.49 | 15.51 | 15.51 | 4.54 | 20.05 | 20.05 | 5.73 | 4.54 | 0.00 | | | |
| CO2 | 0.04 | 0.04 | 3.83 | 3.83 | 1.10 | 4.93 | 4.93 | 1.39 | 1.10 | 0.00 | | | |
| CH4 | 77.36 | 77.36 | 199.76 | 199.76 | 21.59 | 221.34 | 221.34 | 27.40 | 21.59 | 0.00 | 7.60 | 7.60 | 706.00 |
| C2H6 | 0.02 | 0.02 | 16.37 | 16.37 | 7.79 | 24.13 | 24.13 | 18.61 | 7.79 | 8.04 | | | |
| C2H4 | | | | | | | | | | | 66.00 | 66.00 | 66.00 |
| C3H8 | 0.00 | 0.00 | 2.33 | 2.33 | 0.88 | 3.14 | 3.14 | 15.54 | 0.88 | 13.82 | 16.00 | 16.00 | 16.00 |
| IC4H10 | 0.00 | 0.00 | 0.12 | 0.12 | 0.05 | 0.16 | 0.16 | 2.83 | 0.05 | 2.73 | 60.00 | 60.00 | 60.00 |
| NC4H10 | 0.00 | 0.00 | 0.12 | 0.12 | 0.05 | 0.14 | 0.14 | 4.48 | 0.05 | 4.37 | | | |
| IC5H12 | 0.00 | 0.00 | 0.01 | 0.01 | 0.00 | 0.00 | 0.00 | 1.89 | 0.00 | 1.87 | | | |
| NC5H12 | 0.00 | 0.00 | 0.01 | 0.01 | 0.01 | 0.00 | 0.00 | 1.57 | 0.00 | 1.56 | | | |
| NC6H14 | 0.00 | 0.00 | 0.00 | 0.00 | 0.00 | 0.00 | 0.00 | 1.31 | 0.00 | 1.31 | | | |
| | 337.91 | 238.06 | 238.06 | 238.06 | 36.00 | 273.89 | 273.89 | 80.75 | 36.00 | 33.70 | 149.60 | 149.60 | 848.00 |
| TEMP, D-F | −120.00 | 90.00 | −240.00 | −120.00 | −70.00 | −113.00 | 90.00 | −100.00 | −43.40 | 113.00 | 68.50 | 68.50 | 164.00 |
| PRESS, PSIA | 60.00 | 55.00 | 65.00 | 60.00 | 60.00 | 60.00 | 55.00 | 695.00 | 265.00 | 268.00 | 45.00 | 45.00 | 135.00 |
| MASS, LB/HR | 8540 | 8540 | 4418 | 4418 | 801 | 5211 | 5211 | 2693 | 801 | 1624 | 6167 | 6167 | 6167 |
| MOL WT | 25.28 | 25.27 | 18.56 | 18.56 | 22.45 | 19.03 | 19.03 | 33.35 | 22.25 | 48.20 | 41.22 | 41.22 | 41.22 |

| STREAM NO | | | | | | | | | | | | | |
|---|---|---|---|---|---|---|---|---|---|---|---|---|---|
| | 206 | 208 | 212 | 220 | 222 | 226 | 238 | 230 | 224 | 239 | 231 | 232 | 219 |
| PHASE | V | V | V | 2 | 2 | L | 2 | V | V | L | L | L | 2 |
| | MATERIAL BALANCE EXAMPLE (REFRIGERANT) | | | | | | | | | | | | |
| CH4 | 7.60 | 8.76 | 8.76 | 8.76 | 8.76 | 3.16 | 1.16 | 1.16 | 5.61 | 1.99 | 7.60 | 7.60 | 7.60 |
| C2H4 | 66.00 | 83.20 | 83.20 | 83.20 | 83.20 | 46.42 | 17.20 | 17.20 | 36.58 | 29.42 | 66.00 | 66.00 | 66.00 |
| C3H8 | 16.00 | 22.53 | 22.53 | 22.53 | 22.53 | 17.70 | 6.53 | 6.53 | 4.83 | 11.17 | 16.00 | 16.00 | 16.00 |
| IC4H10 | 60.00 | 88.32 | 88.32 | 88.32 | 76.75 | 28.32 | 28.32 | 28.32 | 11.57 | 48.43 | 60.00 | 60.00 | 60.00 |
| | 149.60 | 202.81 | 202.81 | 202.81 | 202.81 | 144.03 | 53.21 | 5321 | 58.59 | 91.01 | 149.60 | 149.60 | 149.60 |
| TEMP, D-F | 120.00 | 118.00 | 233.80 | 171.00 | 115.00 | 115.00 | 57.00 | 105.00 | 115.00 | 115.00 | 115.00 | −100.00 | −107.00 |
| PRESS, PSIA | 132.00 | 132.00 | 450.00 | 445.00 | 440.00 | 440.00 | 137.00 | 134.00 | 440.00 | 440.00 | 440.00 | 435.00 | 45.00 |
| MASS, LB/HR | 6167 | 8602 | 8602 | 8602 | 8602 | 6600 | 2436 | 2436 | 2001 | 4165 | 6166 | 6166 | 6166 |
| MOL WT | 41.22 | 42.41 | 42.41 | 42.41 | 42.41 | 45.76 | 45.76 | 45.76 | 34.16 | 45.76 | 41.22 | 41.22 | 41.22 |

Because many varying and different embodiments may be made within the scope of the inventive concept herein taught including equivalent structures or materials hereafter thought of, and because many modifications may be made in the embodiments herein detailed in accordance with the descriptive requirements of the law, it is to be understood that the details herein are to be interpreted as illustrative and not in a limiting sense.

What is claimed is:

1. A process for separating a nitrogen rich hydrocarbon stream, comprising:
    A. Cooling the nitrogen rich hydrocarbon stream in an indirect heat exchanger with a mixed component refrigerant having at least three components:
    B. Separating heavier naturally occurring hydrocarbons in the nitrogen rich hydrocarbon stream from the rest of the nitrogen rich hydrocarbon stream;
    C. Cooling the lighter components remaining stream in an indirect heat exchange with cooled components of the lighter components remaining stream; and D. Multi-stage flash separating heavier portions of the lighter components remaining stream into a first product stream which is a nitrogen rich, low heating value stream and a second product stream which is a predominately methane gas stream of approximately 1000 BTU content.

2. The process of claim 1, wherein Step B includes the steps of:

E. Separating the nitrogen rich hydrocarbon stream into a lighter components stream and a heavier naturally occurring hydrocarbons stream;

F. Distilling the heavier naturally occurring hydrocarbons to form a hydrocarbon liquid stream and a third product stream;

G. Compressing the mixed component refrigerant stream prior to Step A; and

H. Using the mixed component refrigerant stream to provide heat energy for the distillation, such refrigerant supplying such heat energy prior to the cooling in Step A.

3. The process of claim 2, wherein there is further included the steps of:

I. After Step H, splitting the compressed refrigerant of step G into two portions of different composition; and J. Supplying a first portion of the compressed refrigerant of Step I for cooling in Step A.

4. The process of claim 3, wherein Step G is a two stage compression process and there is included the additional steps of:

K. Feeding the first portion of the compressed refrigerant after Step A to the inlet of the first stage of compression; and L. Feeding the second portion of the compressed refrigerant after Step I to the inlet of the second stage of compression.

5. The process of claim 1, wherein Step B includes the steps of:

M. Flashing the nitrogen rich hydrocarbon stream to form a lighter components remaining stream and a heavier stream;

N. Separating substantial quantities of methane from the heavier stream of Step M; and O. Combining the stream from Step N with the methane gas stream from Step D.

6. The process of claim 1, wherein Step C includes the steps of:

P. Cooling the lighter components remaining stream in a first indirect heat exchanger with cooled components of the lighter components remaining stream; and Q. Cooling the lighter components remaining stream in a second indirect heat exchanger with a cooled heavier portion of the lighter components remaining stream.

7. The process of claim 6, wherein step D includes the steps of:

R. Flashing the effluent cooled lighter components remaining stream of Step Q to form the cooled heavier portion of the lighter components remaining stream and a first lighter portion of the lighter components remaining stream;

S. Recycling the cooled heavier portion of the lighter components remaining stream as the cooling media of Step Q; and T. Flashing the effluent heavier portion of the lighter components remaining stream after Step S to form the predominately methane gas stream of approximately 1000 BTU content and a second lighter portion of the lighter components remaining stream;

U. Combining the first and second lighter portions of the lighter components remaining stream to form the nitrogen rich, low heating value stream.

* * * * *